US00PP25537P3

(12) United States Plant Patent
Kardos

(10) Patent No.: US PP25,537 P3
(45) Date of Patent: May 12, 2015

(54) ***LAGERSTROEMIA* PLANT NAMED 'PIILAG B1'**

(50) Latin Name: ***Lagerstroemia indica*×L. *fauriei***
Varietal Denomination: PIILAG B1

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 13/815,403

(22) Filed: Feb. 28, 2013

(65) Prior Publication Data

US 2014/0245506 P1 Aug. 28, 2014

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

U.S. PATENT DOCUMENTS

| | | | |
|---|---|---|---|
| PP10,319 | P | 4/1998 | Whitcomb |
| PP16,917 | P2 | 8/2006 | Dirr |
| PP17,411 | P2 | 2/2007 | Dirr |
| PP21,540 | P2 | 11/2010 | Knight |
| PP22,161 | P2 | 9/2011 | Dirr |
| PP23,071 | P3 | 9/2012 | Dirr |
| PP23,168 | P3 | 11/2012 | Griffith |
| PP23,178 | P3 | 11/2012 | Dirr |
| PP23,518 | P3 | 4/2013 | Kardos |
| 2013/0125275 | P1 | 5/2013 | Kardos |
| 2013/0125276 | P1 | 5/2013 | Kardos |

OTHER PUBLICATIONS

First Editions Collection webpage, (downloaded Mar. 6, 2013, available on Internet in Jan. 2013), "*Lagerstroemia* 'PIILAG-IV'", http://www_._firsteditionsplants_._com_/collection, 1 page.
First Editions Collection webpage, (downloaded Mar. 6, 2013, available on Internet in Jan. 2013), "*Lagerstroemia* 'PIILAG-V'", http://www_._firsteditionsplants_._com_/collection, 1 page.
American Nurseryman Catalog, "2013_AN_Woody Plants," Dec. 2012, p. W5.

*Primary Examiner* — Kent L Bell
(74) *Attorney, Agent, or Firm* — Lathrop & Gage LLP

(57) ABSTRACT

A new and distinct cultivar of *Lagerstroemia* plant named 'PIILAG B1', characterized by its compact, rounded intermediate growth habit, reddish new growth, lustrous dark green foliage in summer, white flowers, and resistance to powdery mildew and *Cercospora* leaf spot.

2 Drawing Sheets

Genus and species of plant claimed: *Lagerstroemia indica*×L. *fauriei*.

Variety denomination: 'PIILAG B1'.

BACKGROUND OF THE INVENTION

The present invention relates to a new and distinct cultivar of *Lagerstroemia* plant, botanically known as *Lagerstroemia indica*×L. *fauriei*, commonly known as crapemyrtle, and hereinafter referred to by the cultivar name 'PIILAG B1'. 'PIILAG B1' is grown primarily as an ornamental for landscape use and for use as a potted plant.

'PIILAG B1' originated from open-pollinated seed of an unnamed and unpatented seedling known to the inventor as #5 growing in Watkinsville, Ga. The cultivar 'PIILAG B1' originated in 2008 and was selected in a cultivated environment in Watkinsville, Ga. from the progeny of this open-pollination by continued evaluation for growth habit and foliage and flower characteristics.

Asexual reproduction of 'PIILAG B1' by stem cuttings in Watkinsville, Ga. since 2009 has shown that all the unique features of this new *Lagerstroemia*, as herein described, are stable and reproduced true-to-type through successive generations of such asexual propagation.

SUMMARY OF THE INVENTION

Plants of the new cultivar 'PIILAG B1' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG B1'. These characteristics in combination distinguish 'PIILAG B1' as a new and distinct cultivar:

1. Compact, rounded intermediate growth habit;
2. Reddish new growth;
3. Lustrous dark green foliage in summer;
4. White flowers;
5. Resistance to powdery mildew and *Cercospora* leaf spot.

Plants of 'PIILAG B1' differ from plants of the parent, #5, primarily in growth habit and foliage quality. Plants of #5 have a compact, rounded dwarf growth habit and foliage that emerges bright green and matures to medium green, whereas plants of 'PIILAG B1' have an overall larger, compact, rounded intermediate growth habit and foliage that emerges red and matures to lustrous dark green.

Plants of 'PIILAG B1' can be compared to the cultivar 'White Chocolate' (unpatented), but differ in growth habit and foliage color. Plants of 'PIILAG B1' have a compact, rounded intermediate growth habit and foliage that emerges red and matures to lustrous dark green, whereas plants of 'White Chocolate' have an overall larger, rounded growth habit and reddish purple new growth that matures to purplish green.

Plants of 'PIILAG B1' can be compared to the cultivar 'PIILAG-I' (U.S. Plant Pat. No. 23,168), but differ in growth habit and overall size of foliage and flowers. Plants of 'PIILAG B1' have a compact, rounded intermediate growth habit, whereas plants of 'PIILAG-I' have a dwarf, rounded growth habit and overall smaller foliage and flowers.

BRIEF DESCRIPTION OF THE DRAWINGS

The accompanying color photographs illustrate the flower and foliage characteristics and the overall appearance of 'PIILAG B1', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
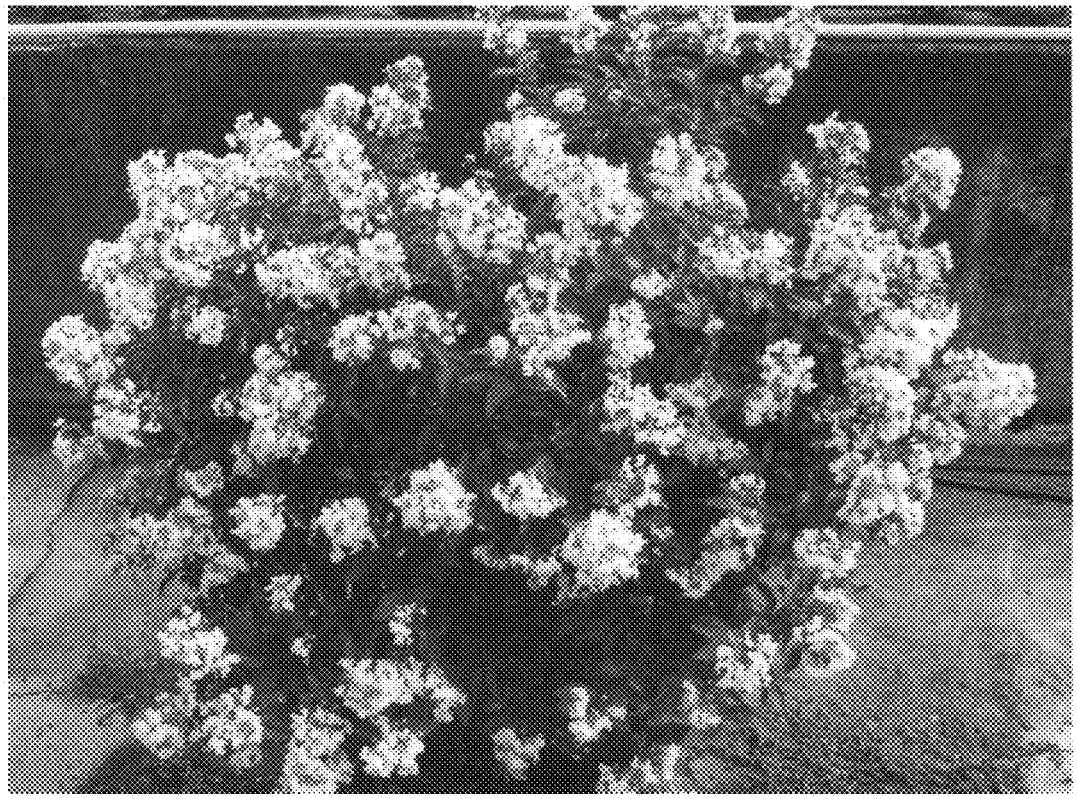
FIG. 1 illustrates the overall appearance of a mature plant of 'PIILAG B1' in a container.
Figure 2:
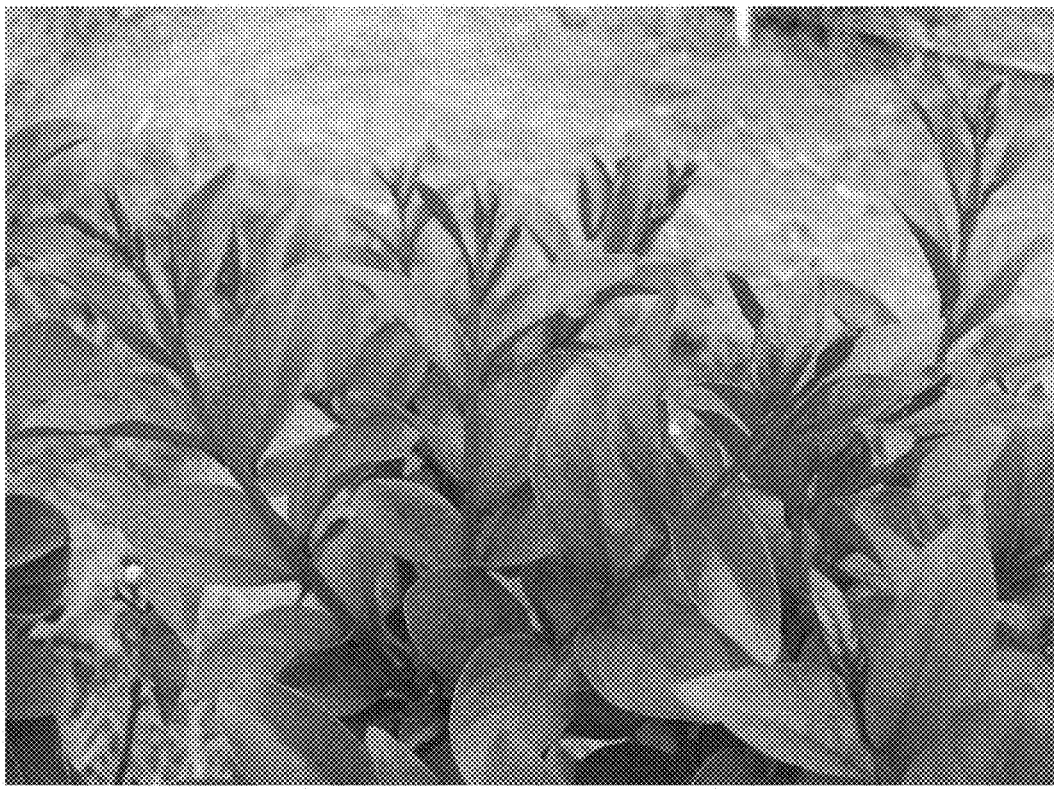
FIG. 2 illustrates a close-up view of the new growth of 'PIILAG B1'.

In the following description, color references are made to The Royal Horticultural Society Colour Chart, 2007 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG B1'.

Parentage:

*Female, or seed, parent.*—*Lagerstroemia* #5 (unpatented).

*Male, or pollen parent.*—Unknown (open-pollinated).

Propagation: Terminal cuttings.

*Time to initiate roots, summer.*—About 21 days at 32° C.

Plant description: Flowering shrub; compact, rounded intermediate growth habit. Freely branching; lateral branches abundant without pruning, resulting in fine-textured, dense habit.

*Root description.*—Numerous, fine, fibrous and well-branched.

*Plant size.*—The original plant, now about five-years-old in the ground, is about 137 cm high from the soil level to the top of the inflorescences and about 122 cm wide. First year stems have a diameter of about 2.5 mm. First year stems have length of 30.48 cm to 45.75 cm. Shape: squarish. Second year and older stems have a diameter of about 5 mm or more. Second year stems have length of 60.96 cm to 91.44 cm. Shape: round.

*Trunk diameter.*—3 cm at the soil line. Color: N199B.

*Internode length.*—About 2.1 cm.

*Strength.*—Flexible when young, easily broken once mature.

*First year stem color* (*young*).—183A. Color (woody): 200D.

*Second year and older stem color.*—N199B.

*Bark.*—Exfoliates in strips beginning on second or third year stems.

Vegetative buds: Sub-opposite to alternate in arrangement, imbricate, conical, with no pubescence.

*Color.*—183B.

*Size.*—About 2.5 mm in length and 1 mm in width.

Foliage description:

*Arrangement.*—Sub-opposite to alternate, simple.

*Length.*—About 5 cm.

*Width.*—About 3 cm.

*Shape.*—Elliptical.

*Apex.*—Acuminate.

*Base.*—Cuneate.

*Margin.*—Entire.

*Texture* (*upper and lower surfaces*).—Glabrous and glossy.

*Venation pattern.*—Pinnate.

*Venation color of emerging foliage* (*upper and lower surfaces*).—180A.

*Venation color of fully expanded foliage* (*upper and lower surfaces*).—47A.

*Color in developing foliage* (*upper and lower surfaces*).—180A.

*Color in fully expanded foliage* (*upper surface*).—147A.

*Color in fully expanded foliage* (*lower surface*).—147B.

*Petiole length.*—About 2 mm.

*Petiole diameter.*—About 1 mm.

*Petiole color* (*upper and lower surfaces*).—177A.

*Pubescence.*—None.

Flower description: Flowers are produced from about June to September in Watkinsville, Ga. An inflorescence is showy for about two weeks, and individual flowers last about one day and are self-cleaning. Flowers are lightly fragrant.

*Inflorescence type.*—Panicle. Panicle contains between 20 to 150 buds or flower.

*Inflorescence length.*—About 12 cm.

*Inflorescence width.*—About 9.5 cm.

*Peduncle.*—About 10 cm in length, about 2 mm in diameter, color is 178B, and no pubescence.

*Individual flowers.*—About 2.2 cm in height and 3.7 cm in diameter.

*Flower buds.*—Length: about 8 mm; Diameter: about 8 mm; Color: 39D. Unopened flower buds are globose with six distinct lines of dehiscence where they split to reveal the flower.

*Sepals.*—Arrangement/quantity: single whorl of six fused sepals. Length: about 9 mm. Width: about 4 mm. Shape: elliptical. Apex: acute. Margin: entire. Texture, upper and lower surfaces: smooth, glabrous. Color when opening, upper surface: 37B. When opening, lower surface: 144C. Fully opened, upper surface: 37B. Fully opened lower surface: 144C.

*Pedicels.*—About 7 mm in length, 1 mm in diameter, 178B in color, and no pubescence.

*Calyx.*—About 9 mm in length, about 1.1 cm in diameter, 36A in color on both surfaces, and no pubescence.

Petals:

*Arrangement/appearance.*—Usually 6 or 7 per flower.

*Petal length.*—About 1.9 cm.

*Petal width.*—About 1.3 cm.

*Petal shape*.—Fan-shaped.
*Petal apex*.—Ruffled, rounded.
*Petal base*.—Sagittate.
*Petal margin*.—Undulate.
*Petal texture* (*upper and lower surfaces*).—Glabrous.
*Petal color*.—Upper and lower surfaces are 155C.

Stamens:

*Quantity/arrangement*.—About 25 to 30 short stamens clustered in the center, about 8 mm long, filament color is 2C, and anther color is 13A. The short stamens are surrounded by 6 longer stamens, about 1.2 cm long, filament color is 63A, and anther color is N199C. The stamens are not pubescent.
*Pollen*.—Produced in moderate quantities and is 13B in color on the short stamens and 144C in color on the long stamens.

Pistils:

*Quantity*.—One superior pistil per flower.
*Pubescence*.—None.
*Pistil length*.—About 1.9 cm in length.
*Stigma shape*.—Round, about 1 mm in diameter.
*Stigma color*.—146B.
*Style color*.—178D and about 1.6 cm in length.
*Ovary color*.—5D and about 2 mm in diameter.

Fruit:

*Type/appearance*.—Six-valved, dehiscent, broad ellipsoidal capsule.
*Length*.—About 8 mm.
*Diameter*.—About 7 mm.
*Immature color*.—144A.
*Mature color*.—200C. Each capsule contains many seeds that are about 5 mm long, 3 mm wide, and 200C in color.

Plant hardiness:

*Plant hardiness*.—USDA Plant Hardiness Zone Map (2012): Zone 6 to 9.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG B1', as illustrated and described herein.

* * * * *